(12) United States Patent
Kadir et al.

(10) Patent No.: US 8,682,044 B2
(45) Date of Patent: Mar. 25, 2014

(54) METHODS OF ANALYZING AND CORRECTING MEDICAL IMAGING DATA

(75) Inventors: Timor Kadir, Oxford (GB); Matthew David Kelly, Botley (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 783 days.

(21) Appl. No.: 12/575,637

(22) Filed: Oct. 8, 2009

(65) Prior Publication Data

US 2010/0092051 A1 Apr. 15, 2010

(30) Foreign Application Priority Data

Oct. 9, 2008 (GB) .................................. 0818490.5

(51) Int. Cl.
*G06K 9/00* (2006.01)

(52) U.S. Cl.
USPC ........................................................ 382/128

(58) Field of Classification Search
USPC ................................................ 382/128–132
See application file for complete search history.

(56) References Cited

U.S. PATENT DOCUMENTS

| 4,947,412 | A | 8/1990 | Mattson |
| 5,841,832 | A | 11/1998 | Mazess et al. |
| 6,251,362 | B1 * | 6/2001 | Wahl et al. .................... 424/1.11 |
| 6,259,761 | B1 | 7/2001 | Lai |
| 2004/0081270 | A1 | 4/2004 | Heuscher |
| 2005/0288869 | A1 * | 12/2005 | Kroll et al. ...................... 702/19 |
| 2007/0092055 | A1 | 4/2007 | Vives et al. |
| 2007/0160276 | A1 | 7/2007 | Chen et al. |
| 2007/0165920 | A1 * | 7/2007 | Gering et al. .................. 382/128 |
| 2008/0230703 | A1 * | 9/2008 | Kadrmas et al. .......... 250/363.03 |
| 2010/0023345 | A1 * | 1/2010 | Schottlander ...................... 705/2 |

OTHER PUBLICATIONS

Nichols et al., "Spatiotemporal Reconstruction of List-Mode PET Data, IEEE Trans. on Medical Imaging", vol. 21, No. 4, Apr. 2002, pp. 396-404.

* cited by examiner

*Primary Examiner* — Elaine Gort
*Assistant Examiner* — Jonathan K Ng
(74) *Attorney, Agent, or Firm* — Schiff Hardin LLP

(57) ABSTRACT

In a method and apparatus for analyzing and correcting medical imaging data of a subject, an image data set is obtained from a scan of the subject at a first time point with respect to a defined time origin. A measurement of a time-dependent variable is then determined for the data set, and an estimated value for the time-dependent variable at an estimate time point is extrapolated from the data set.

11 Claims, 3 Drawing Sheets

FIG 2
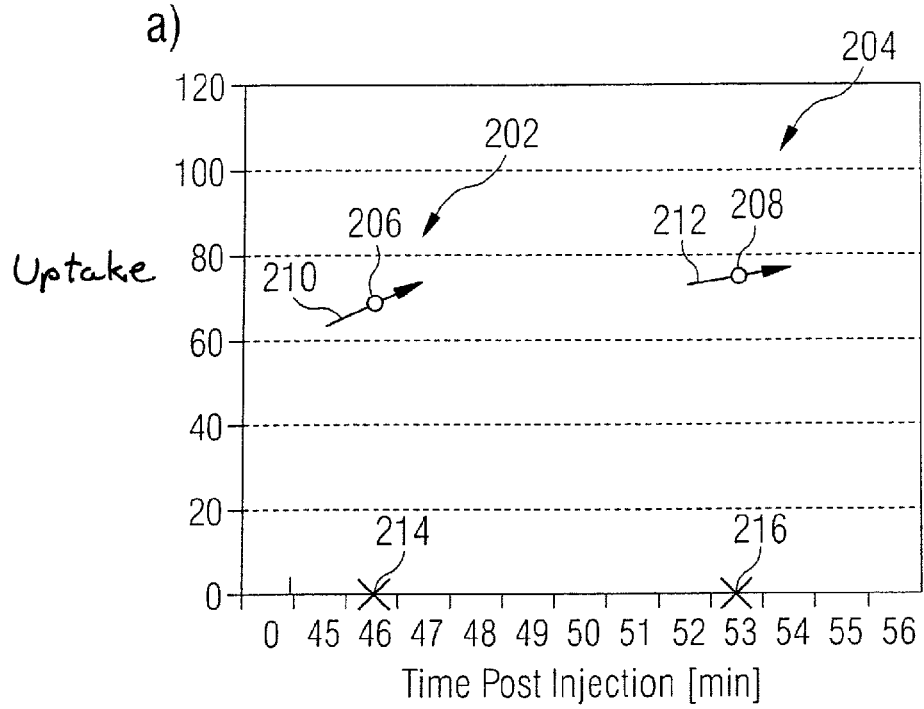
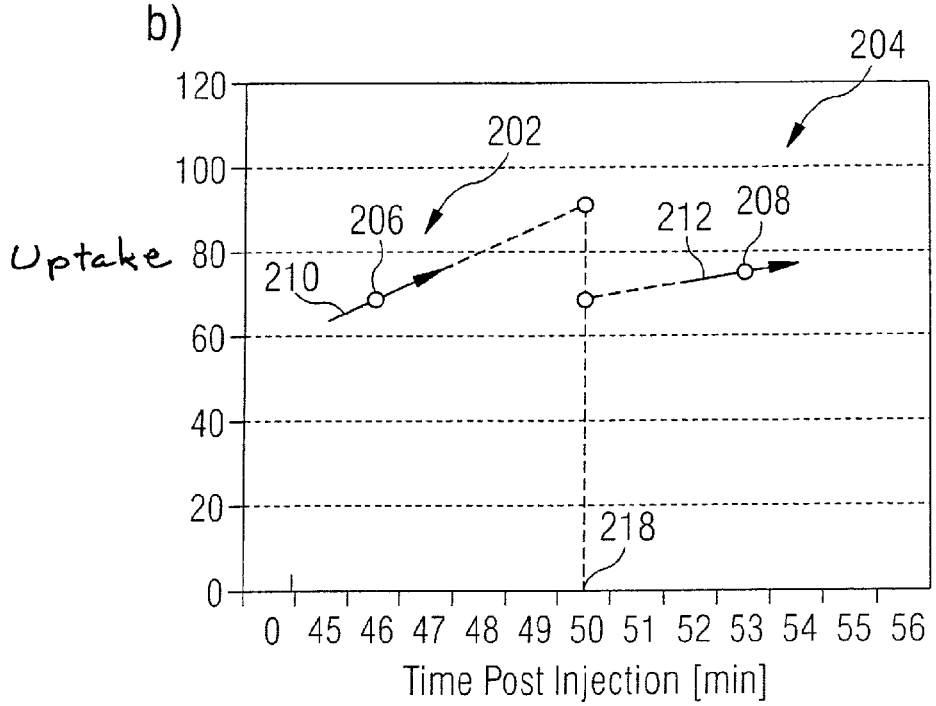

METHODS OF ANALYZING AND CORRECTING MEDICAL IMAGING DATA

BACKGROUND OF THE INVENTION

1. Field of the Invention

This invention concerns methods and apparatuses for analyzing and correcting medical imaging data of a subject.

2. Description of the Prior Art

In the medical imaging field, several nuclear medicine emission imaging schemes are known. For example PET (Positron Emission Tomography) is a method for imaging a subject in 3D using an ingested radio-active substance which is processed in the body, typically resulting in an image indicating one or more biological functions. FDG, for instance, is a glucose analog which is used as the radiopharmaceutical tracer in PET imaging to show a map of glucose metabolism. For cancer for example, FDG is particularly indicated as most tumors are hypermetabolic, which will appear as a high intensity signal in the PET image. For this reason, PET imaging is widely used to detect and stage a wide variety of cancers. The level of glucose activity is usually highly correlated with the aggressiveness and extent of the cancer, and, for example, a reduction in FDG signal between a baseline and a follow-up scan is often indicative of a positive response to therapy.

A key criterion used in evaluating suspicious lesions in a PET scan is the Standardized Uptake Value (SUV). This value is computed from the number of counts of emission events recorded per voxel in the image reconstructed from the event data captured in the PET scan (coincidence emission events along the line of response). Effectively the SUV's purpose is to provide a standardized measure of the spatial distribution of radiotracer concentration throughout the imaged portion of the body.

Conventionally, PET scans are acquired using a static protocol, producing a single image volume representing the average counts (per voxel) detected over a fixed period of time following a given interval between radiotracer injection and image acquisition.

The interval between radiotracer injection and PET acquisition is intended to allow the biological system to reach a steady state equilibrium, with respect to radiotracer distribution. However, with many clinical protocols using an interval of 45-60 mins for 18F-FDG, this equilibrium is often not achieved. As such, small differences in the timing of the acquisition window, post injection (PI) of radiotracer, can significantly affect the uptake (or SUV) measured for a malignant region.

Despite this fact, variations occur in the PI interval during the clinical imaging process, which may in turn result in the misinterpretation of a difference in uptake (or SUV) between two scans, when in fact it may purely be as a result of different PI intervals.

Currently, efforts are made to maintain consistency in PI interval in a clinical protocol, but variations do still occur as not all factors can be controlled. Despite these variations, typically no attempts to correct for the potential impact of such differences are made; furthermore, the clinician reading the scan is often unaware of such differences.

Some clinical applications that can simultaneously load multiple data volumes highlight to the user any significant differences in the PI interval between the two scans have been previously considered (for example, TrueD from Siemens Healthcare). However, this is only intended to inform the user that such a different exists and does not attempt to correct for the uptake itself.

SUMMARY OF THE INVENTION

An object of the present invention is to address these problems and provide improvements upon the known devices and methods.

In general terms, one embodiment of a first aspect of the invention can provide a method of analyzing medical imaging data of a subject, includes obtaining a first image data set from a scan of the subject at a first time point with respect to a defined time origin, determining a first measurement of a time dependent variable for the first data set, and extrapolating from the first data set a first estimate value for the time dependent variable at a first estimate time point.

Thus an estimate of a value for the variable can be made at a time point other than that of the data set in question, so that a different PI interval can be accounted for.

Preferably, the step of extrapolating includes extrapolating the first estimate value from the first measurement of the time dependent variable, and a calculated rate of change of the variable for the first data set.

The method can further include obtaining a second image data set from a scan of the subject at a second time point with respect to the defined time origin, determining a second measurement of a time dependent variable for the second image data set, and comparing the first estimate value for the variable with the second measurement of the variable. This allows a comparison of a value at a different time point, for example a different PI interval, to be made.

In an embodiment, the first estimate time point is the second time point.

In another embodiment, the step of comparing with the second measurement includes extrapolating from the second data set a second estimate value for the time dependent variable at the first estimate time point, and comparing the first and second estimate values.

In yet another embodiment, the step of comparing includes extrapolating the second estimate value at a third time point intermediate the first and second time points. The method then further includes extrapolating first, second and third estimate values at each of the first, second and third time points, and comparing the first, second and third estimate values.

More preferably, the step of extrapolating includes obtaining from the first data set a plurality of measurements of the time dependent variable within a period of the scan at a given region of the imaging volume, establishing a sub-period time point within the scan period for each such measurement, calculating from the measurements and the sub-scan time points a rate of change of the variable for the given region, and extrapolating the estimate value for the variable according to the calculated rate of change.

The number of measurements of the time dependent variable can be a count of emission events captured by an imaging apparatus.

Preferably, the time dependent variable is uptake of a tracer.

In one embodiment, the first data set is obtained from a first scan of the subject at the first time point, and the second data set is obtained from a second scan of the subject at the second time point.

In an alternative embodiment, the first data set and the second data set are obtained from the same scan of the subject. This allows comparison of different time points within the same scan subject matter, for example to compare different regions of interest, or different tissues types.

More preferably, the method further includes using the first estimate value for the time dependent variable at the estimate time point to correct a value for the uptake of a tracer for the medical imaging data.

In an embodiment, the method further includes using the first estimate value to modify a value for the uptake of a tracer for the medical imaging data. This allows an uptake value to be modified or corrected on the basis of the extrapolation, so that, for example, an uptake value established at a first PI interval can be altered to indicate what the uptake value would be at a second PI interval.

In a further embodiment of the invention, a method of analyzing medical imaging data of a subject captured by a medical imaging apparatus includes obtaining, by a processor, a first image data set from a scan of the subject by the imaging apparatus at a first time point with respect to a defined time origin, determining, by a processor, a first measurement of a time dependent variable for the first data set, extrapolating, by a processor, from the first data set a first estimate value for the time dependent variable at a first estimate time point, and displaying the first estimate value on a display device.

In another embodiment of the invention, an apparatus for analyzing medical imaging data of a subject captured by a medical imaging apparatus has a processor that obtains a first image data set from a scan of the subject by the imaging apparatus at a first time point with respect to a defined time origin, determines a first measurement of a time dependent variable for the first data set, and extrapolates from the first data set a first estimate value for the time dependent variable at a first estimate time point, and a display device that displays the first estimate value.

In another embodiment of the invention, a method of correcting medical imaging data of a subject captured by a medical imaging apparatus, includes obtaining, by a processor, a first image data set from a scan of the subject by the imaging apparatus at a first time point with respect to a defined time origin, determining, by a processor, a first measurement of a time dependent variable for the first data set, extrapolating, by a processor, from the first data set a first estimate value for the time dependent variable at a first estimate time point, using the first estimate value for the time dependent variable at the estimate time point to correct, by a processor, a value for the uptake of a tracer for the medical imaging data, and displaying the corrected value on a display device.

The invention can also encompasses a computer-readable medium encoded with computer program codes that when the medium is loaded into or run on a computer, causes the computer to implement a method, according to any of the above described embodiments.

BRIEF DESCRIPTION OF THE DRAWINGS

FIG. 2 is a diagram illustrating the extrapolation of uptake values from different scans according to an embodiment of the invention.

DESCRIPTION OF THE PREFERRED EMBODIMENTS

When the following terms are used herein, the accompanying definitions can be applied:

PET—Positron Emission Tomography
ROI—Region of Interest
VOI—Volume (Region) of Interest
FDG—2-18F-Fluoro-2-deoxy-D-glucose
AUC—Area Under the Curve
SUV—Standardized Uptake Value
TAC—Time-Activity Curve
PI—Post Injection In an embodiment, the present invention attempts to correct measured ROI intensity/SUV for variations in PI interval using the estimate of the slope of the underlying TAC. This slope can be computed using the methodology described in GB 0818495.4 and another co-pending UK application (attorney reference: 2008P19156 GB01), and summarized in the following description.

The method of this embodiment is as follows:

1. Compute a slope estimate (using the methodology described in below) for the region of interest (ROI) corresponding to the physiological feature being studied (e.g., a malignant lesion) from each scan being compared.

2. Identify a difference in PI interval based on information in the DICOM header (i.e., 0054,0016: Radiopharmaceutical Information Sequence).

3. Extrapolate (linearly) the measured intensity/SUV from each scan to a common time point based on the computed slope values and PI intervals (see FIG. 2).

Figure 1:
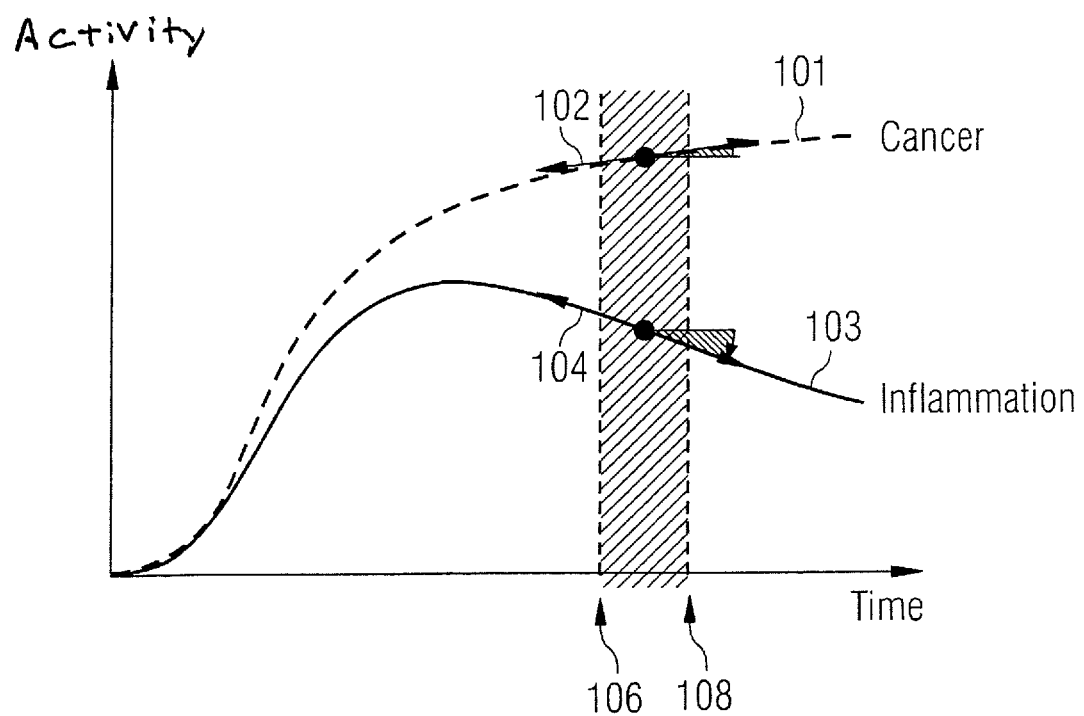
FIG. 1 is a schematic illustration of the calculation of derivatives of time activity curves for a PET scan according to an embodiment of the invention.

Briefly, the slope estimate methodology essentially computes a derivative image which allows calculation of the change of uptake over time. With reference to FIG. 1, the acquisition scan is between time points 106 and 108, and curves 101 and 103 are the TACs for two different tissue areas. Conventional image processing would usually measure the average of uptake over the scan time period (i.e. a flat line across the scan period 106 to 108). In this methodology, the derivative slopes 102 and 104 for the change of uptake over the acquisition period are derived.

The differing slopes can identify the different tissues types as cancerous and inflamed. If the rate of uptake is increasing, as in cancer, the derivative image should have a positive signal. Otherwise, if the rate is decreasing, as for inflammation, the signal would be negative. Differentiation between malignancy and inflammation, or other non-malignant tissues with high uptake, may therefore be facilitated.

A simple method of calculating this derivative is, rather than averaging an uptake value across the entire scan period, to compute a series of images from the same list-mode data by resampling time in small intervals: for instance, from a 10 minute list-mode scan, 10 1-minute images can be reconstructed (or 5 2-minutes images, etc). From these 10 1-minute divisions, the 10 values of the signal at a specific point can be fitted with a line, and the slope of the line is therefore an estimate of the derivative.

Returning to the present embodiment of the invention, FIG. 2 is an illustration of an extrapolation method for time-correcting intensities/SUVs. With reference to FIG. 2(a), a first scan result (202) and a second scan (204) result for the ROI in question are shown. An intensity or uptake value (206, 208 respectively) is obtained for each scan, and a gradient (210, 212) is derived for each, using the slope estimating methodology described immediately above. Using the uptake and slope for each scan's ROI, along with the respective PI interval (214, 216), the intensities can be extrapolated (FIG. 2(b)) to a common time point 218 (i.e., 50 mins in this example).

This approach assumes the underlying TAC over the period being extrapolated can be approximated as a linear function. Given static scans are typically acquired after a 45-60 min PI interval (for 18F-FDG), where a second derivative of the TAC is approximately zero, and provided the time interval being extrapolated over is relatively short, this assumption should be valid (alternatives to this assumption are described later).

The extrapolated values from each scan can then be compared with one another graphically (e.g., using the multi-time-point facility of TrueD), or used to scale the image intensity values in the displayed image volume.

An additional application of this method is to adjust the SUVs from a whole body scan to a common time point. Since the whole body is acquired from multiple, sequential, bed positions, the SUVs measured will represent different portions of the underlying TAC and therefore may not be directly comparable. By projecting each SUV to a common time point, this variation may be corrected.

The following sets out a detailed example for this embodiment of the invention.

Consider, for example, two PET/CT scans acquired of the same subject, one month apart. In each scan, the same lesion is visible and a comparison of the measured uptake (e.g., SUV) for the lesion between scans is to be performed. In the first scan the measured lesion uptake is 5 SUV, while in the second scan the measured lesion uptake is 4.5 SUV. However, the first scan was acquired with a post injection interval (PI) of 60 min (i.e. started at a PI of 60 min), whereas the second scan was acquired with a PI of 40 min. The difficulty in such a case is in determining whether the observed difference in SUV is due to a physiological change in the underlying lesion or the difference in post injection intervals.

To address this problem, this embodiment of the invention makes use of the rate of change of SUV that was calculated for the lesion at each time point using the slope estimate methodology described above. In this example, the rate of change of SUV for the first scan (302, FIG. 3) is 0.02 SUV.min−1 and for the second scan (304, FIG. 3) is 0.04 SUV.min−1.

Figure 3:
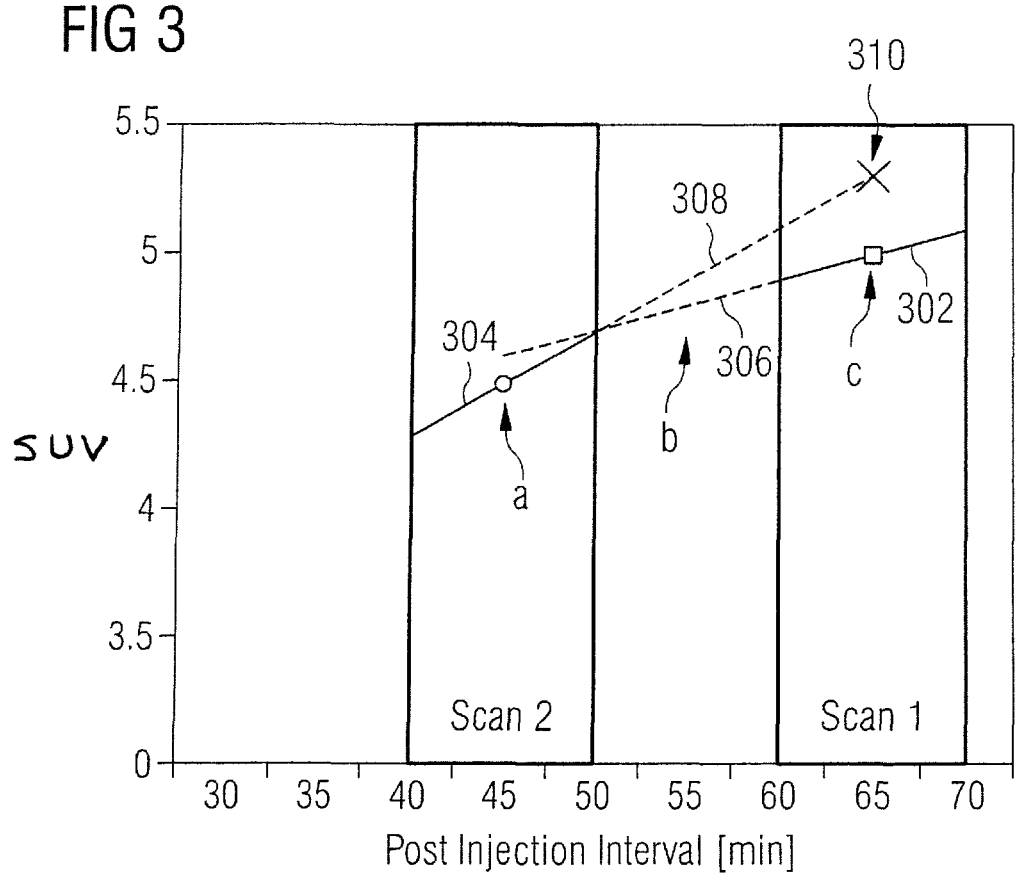
FIG. 3 is a diagram illustrating in detail the extrapolation of uptake values from different scans according to an embodiment of the invention.

FIG. 3 is a diagram illustrating integration of rate of change data into the comparison of measured uptake values acquired from static acquisitions at different post injection intervals (PI).

The measured uptake in scan 1 is linearly extrapolated (dash-dot-dash line 306) based on the measured rate of change (302), as far as the PI of scan 2 (arrow a) through an intermediate PI (arrow b). The measured uptake in scan 2 is also linearly extrapolated (dashed line 308) as far as the same PIs and the PI of scan 1 (arrow c).

FIG. 3 demonstrates the impact of the measured rates of change of SUV (302, 304) on the comparison of lesion uptake. Although the SUV value for scan 2 is lower (4.5 SUV) than for scan 1 (5 SUV), linear extrapolation of the SUV from scan 2 to the PI corresponding to scan 1, based on the measured gradient (308), suggests the SUV at scan 2 may in fact have been higher (supposed point 310) if acquired at the same PI as for scan 1 (arrow c in FIG. 3).

In this example, the linearly extrapolated SUV for a different PI is computed simply as follows:

$$SUV^* = SUV + [(PI^* - PI) \cdot R] \qquad [1]$$

where SUV* is the extrapolated value of the originally measured SUV, PI* is the new PI at which SUV* is to be calculated, and R is the measured rate of change of uptake.

Extrapolation of the SUVs from both scans to an intermediate PI (arrow b in FIG. 3), suggests the SUV from scan 2 would still be greater at this time point. These findings may suggest to the clinician that care may be required with the original results, which appeared to show a drop in SUV between the two scans from 5 to 4.5 SUV.

However, as a further example in this case, if the SUV from scan 1 is extrapolated to the PI of scan 2, it would appear than scan 1 would now have the higher SUV, at this time point. Since the rate of change of uptake is not linear over extended periods, care should be taken when extrapolating over large periods; however, incorporation of rate of change information can highlight situations where additional caution is required when assessing physiological change in uptake between scans.

Of course, in other cases, it may be that all three such extrapolations "agree" that one SUV should indeed be higher than the other, and indeed in still others, the extrapolations may indicate that an original result (e.g. a drop in SUV between scans) was likely correct.

In embodiments of the invention, the common PI interval time point to which measured intensities are corrected may be selected as one of the following:

a. Intermediate time point—the time point equidistant from both acquisitions, or in the case of multiple time points, the mean time point (such as point b in FIG. 3).

b. Original time point—one of the original time points (such as point a or point c in FIG. 3); i.e., all measured intensities are extrapolated to one of the time points acquired (one remains unchanged).

c. Multiple time points—each measured intensity can be extracted to a number of different time points (either intermediate or original), with the range of differences in the corrected intensities/SUVs being used as a measure of error or confidence.

In an alternative, instead of an assumed simple linear rate of change of SUV, the measured intensities may be extrapolated by a non-linear function, for example using the relevant portion of a reference time-activity curve.

The methods described can be used to correct values of uptake of a tracer, and/or can be used as a quality control guide for a clinician. For example, in a simple case, one uptake value could be extrapolated to the time point of a second uptake value for a different scan; if the values disagree, a problem with one or other value may be noted.

Following correction of intensity/SUV in a set of scans, the corrected values may be shown graphically, e.g., a line graph with the original and corrected values to aid the clinician in their interpretation of the data and aid their awareness of the estimated influence of differences in PI interval in the observed changes in intensity/SUV for a given region/lesion.

Alternatively, when one or more regions have been segmented in the scans for tracking (e.g., liver lesion and liver parenchyma) the computed correction factors can be used to scale the displayed images to provide a visual indication of changes in intensity between the PI times considered.

As an alternative to a graphical representation, SUV values being compared from different scans are presented in tabular form using this extrapolation method to compute upper and lower bounds on the differences. For example, when comparing two scans these bounds can be computed (i) by projecting both SUV values to an intermediate time point, (ii) projecting the first value to the time point of the second, and (iii) projecting the second value to the time point of the first. From these values, the biggest and smallest differences would represent the bounds.

In an alternative application of the methods described above, the (at least) two different time points may be in the same scan, for different tissue types. The resultant comparison and/or correction are in such case between these tissue types. For example, in a single scan, scan periods 1 and 2 in FIG. 3 could instead represent sub-periods of the scan addressing different regions of interest, for example the heart at 40 mins, and the bladder at 42 mins. Extrapolation between the two gives an indication of whether uptake has altered in the time between the scans of the different regions of interest, and allows correction for this time lag.

In another alternative, the same method can be used in a case where, rather than the difference between uptake values not being known, the unknown is the PI interval for one of the scans. Thus, where the uptake values are known, and a rate of change for each of the uptake values can either be derived or assumed, a first known PI interval can be used to estimate what the missing or suspect PI interval for a first scan was.

In a further alternative, as opposed to using the slope derived from the methodology described in GB 0818495.4, any temporally-binned data may be used to estimate a slope (e.g., from a dynamic scan, or from a dual time point scan).

In addition to PET, these methods may be applied to any imaging modality for which information about the body is collected dynamically, but generally presented as a static image (e.g., SPECT).

Figure 4:
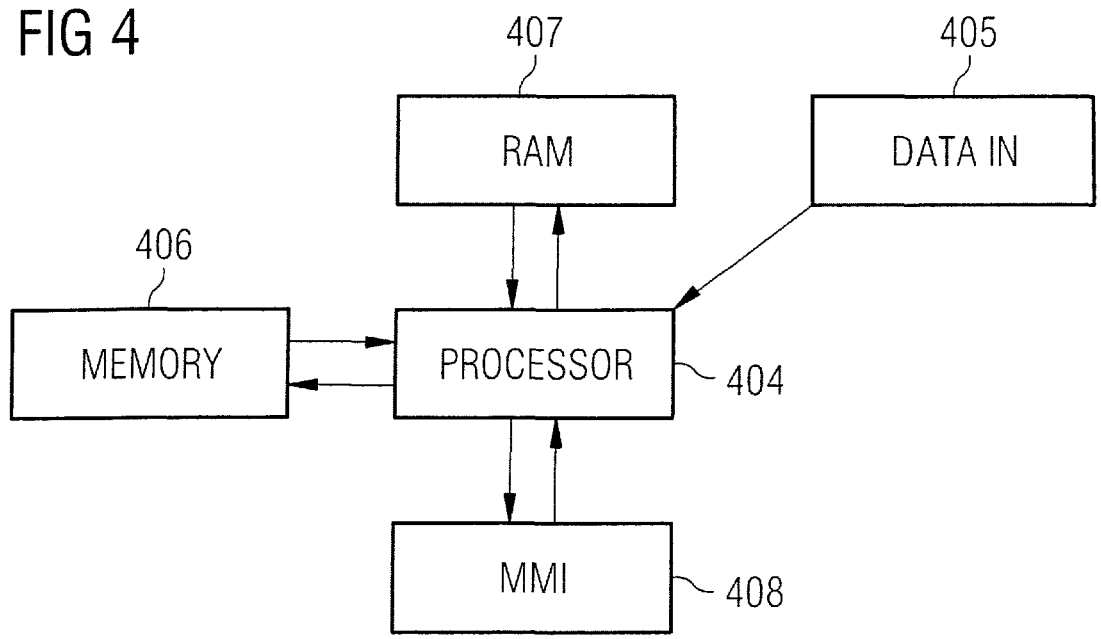
FIG. 4 is a diagram illustrating an apparatus according to an embodiment of the invention.

Referring to FIG. 4, the above embodiments of the invention may be conveniently realized as a computer system suitably programmed with instructions for carrying out the steps of the methods according to the invention.

For example, a central processing unit 404 is able to receive data representative of medical scans via a port 405 which could be a reader for portable data storage media (e.g. CD-ROM); a direct link with apparatus such as a medical scanner (not shown) or a connection to a network.

Software applications loaded on memory 406 are executed to process the image data in random access memory 407.

A Man-Machine interface 408 typically includes a keyboard/mouse/screen combination (which allows user input such as initiation of applications) and a screen on which the results of executing the applications are displayed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for computer-assisted evaluation of medical images, comprising:
    providing a computer with multiple data sets, each representing a respective medical image, each of said data sets comprising data representing a time-dependent variable in the respective medical images, said variable changing over time in the respective medical images with respect to a time origin that is common to the respective medical images, and at least two of said data sets being respectively obtained at different points in time with respect to said time origin;
    in said computer, automatically determining a measurement value of said time-dependent variable in a first of said at least two data sets for a first point in time at which said first of said at least two data sets was obtained;
    in said computer, automatically determining a measured value of said time-dependent variable in a second of said at least two data sets for a second point in time at which said second of said at least two data sets was obtained, said second point in time being after said first point in time;
    in said computer, automatically extrapolating an estimated value of said time-dependent variable in said first of said at least two of said data sets from the second measurement of the time dependent variable; and a calculated rate of change of the variable with respect to time in the second data set over a time duration between said first time and said second time, and identifying a difference between said measured value of said time-dependent variable in said first of said at least two of said data sets and said estimated value; and
    in said computer, generating a visual presentation, at a display screen in communication with said computer, of at least said second of said at least two data sets, with intensity values therein scaled dependent on said difference.

2. A method according to claim 1, wherein the step of extrapolating comprises: obtaining from the first data set a plurality of measurements of the time dependent variable within a period of the scan at a given region of the imaging volume; establishing a sub-period time point within the scan period for each such measurement; calculating from the measurements and the sub-scan time points a rate of change of the variable with respect to time for the given region; and extrapolating the estimate value for the variable according to the calculated rate of change.

3. A method according to claim 2, wherein the plurality of measurements of the time dependent variable is a count of emission events captured by an imaging apparatus.

4. A method according to claim 1 comprising extrapolating the second estimate value at a third point in time intermediate the points in time.

5. A method according to claim 4, further comprising extrapolating first, second and third estimate values at each of the first, second and third time points, and comparing the first, second and third estimate values.

6. A method according to claim 1, comprising using uptake of a tracer by a patient from whom the first and the second of said data sets were obtained the time dependent variable is uptake of a tracer.

7. A method according to claim 1, comprising obtaining the first and the second of said data sets from the same scan of the subject.

8. A method according to claim 7, further comprising using the first estimate value for the time dependent variable at the estimate time point to correct a value for the uptake of said tracer.

9. A method according to claim 7, further comprising using the first estimate value to modify a value for the uptake of said tracer for the medical imaging data.

10. An apparatus for computer-assisted evaluation of medical images, comprising:
    a computer having an input configured to receive multiple data sets, each representing a respective medical image, each of said data sets comprising data representing a time-dependent variable in the respective medical images, said variable changing over time in the respective medical images with respect to a time origin that is common to the respective medical images, and at least two of said data sets being respectively obtained at different points in time with respect to said time origin;
    said computer being configured to automatically determine a measurement value of said time-dependent variable in a first of said at least two data sets for a point in time at which said first of said at least two data sets was obtained;
    said computer being configured to automatically determine a measured value of said time-dependent variable in a second of said at least two data sets for a second point in time at which said second of said at least two data sets was obtained, said second point in time being after said first point in time;
    said computer being configured to automatically extrapolate an estimated value of said time-dependent variable in said first of said at least two of said data sets from the second measurement of the time dependent variable;

and a calculated rate of change of the variable with respect to time in the second data set over a time duration between said first time and said second time, and to identify a difference between said measured value of said time-dependent variable in said first of said at least two of said data sets and said estimated value;

a display in communication with said computer; and said computer being configured to generate a visual presentation, at said display, of at least second of said at least two data sets, with intensity values therein scaled dependent on said difference.

11. A non-transitory, computer-readable data storage medium encoded with programming instructions, said storage medium being loaded into a computer, and said programming instructions causing said computer to:

receive multiple data sets, each representing a respective medical image, each of said data sets comprising data representing a time-dependent variable in the respective medical images, said variable changing over time in the respective medical images with respect to a time origin that is common to the respective medical images, and at least two of said data sets being respectively obtained at different points in time with respect to said time origin;

determine a measurement value of said time-dependent variable in a first of said at least two data sets for a point in time at which said first of said at least two data sets was obtained;

determine a measured value of said time-dependent variable in a second of said at least two data sets for a second point in time at which said second of said at least two data sets was obtained, said second point in time being after said first point in time;

extrapolate an estimated value of said time-dependent variable in said first of said at least two of said data sets, said second point in time being after said first point in time, and identify a difference between said measured value of said time-dependent variable in said first of said at least two of said data sets and said estimated value; and generate a visual presentation, at a display screen, of at least said second of said at least two data sets with intensity values therein scaled dependent on said difference.

* * * * *